United States Patent [19]
Wise et al.

[11] Patent Number: 5,977,176
[45] Date of Patent: Nov. 2, 1999

[54] COMPOSITIONS FOR THE TREATMENT OF WARTS AND HERPES

[76] Inventors: Ronald D. Wise, 9037 Kildare Ave., Skokie, Ill. 60076; Predrag Konstantinovic, 376 Trinity La., Oakbrook, Ill. 60521

[21] Appl. No.: 08/752,676

[22] Filed: Nov. 19, 1996

Related U.S. Application Data

[63] Continuation-in-part of application No. 08/495,219, Jun. 27, 1995, Pat. No. 5,576,005.
[51] Int. Cl.$^6$ .......................... A61K 31/19; A61K 31/56; A61K 31/62
[52] U.S. Cl. ......................... 514/568; 514/171; 514/161
[58] Field of Search .................................. 514/568, 171, 514/161

[56] References Cited

U.S. PATENT DOCUMENTS 5,549,901  8/1996  Wright ..................................... 424/401

OTHER PUBLICATIONS

Morzycka et al 77CA!109871a 1972.
Vachg 117CA!143431m 1992.
Contact dermatitis from propolis, J.A. Raton, A. Aguirre and J.L. Diaz–Perez, *Contact Dermatitis*, 1990, pp. 183–184.
Propolis allergy: A cause of oral mucositis with ulceration, K.D. Hay, BDS, FDSRCS, MDSc, and D.E. Greig, BSc, MMedSc, MB, ChB, FRACP, Grafton, Auckland, New Zealand, *Oral Surg. Oral Med Oral Pathol*, Nov. 1990, pp. 584–586.
Propolis allergy, (l). Origin, properties, usage and literature review, B.M. Hausen, E. Wollenweber, H. Senff and B. Post, *Contact Dermatitis*, 1987, pp. 163–170.
Contact Dermatitis in Beekeepers Due To Propolis (Bee Glue), Mary H. Bunney, *Br. J. Derm*, 1968, 17–23.
Contact dermatitis from propolis, Birgitte Wanscher, *British Journal of Dermatology*, 1976, pp. 451–455.
Contact dermatitis from propolis, F. Kokelj and G. Trevisan, p. 518, *Contact Dermatitis*, 6, 1983.
The incidence of allergy to propolis in 605 consecutive patients patch tested in Prague, J. Machackova, *Contact Dermatitis*, 1988, pp. 210–212.
Occupational dermatitis in a bee–keeper, M.C. Melli, S. Giorgini and A. Sertoli, pp. 427–428, *Contact Dermatitis*.
Contact dermatitis from propolis: role of gastrointestinal absorption, G. Trevisan and F. Kokelj, pp. 48–49, *Contact Dermatitis*.
Sensitivity to propolis, E. Young, pp. 49–50, *Contact Dermatitis*.
Synergistic Effect of Flavones and Flavonols Against Herpes Simplex Virus Type 1 in Cell Culture. Comparison With The Antiviral Activity of Propolis, M. Amoros, C.M.O. Simoes, L. Girre, *Journal of Natural Products*, vol. 55, No. 12, pp. 1732–1733, Dec. 1992, pp. 1732–1740.

*Primary Examiner*—Russell Travers
*Attorney, Agent, or Firm*—Barnes & Thornburg; Alice O. Martin

[57] ABSTRACT

Compositions comprising propolis, propolis and salicylic acid, or propolis and either a corticorsteroid such as hydrocortisone or a halogenated corticosteroid with or without salicylic acid, are effective in the treatment of warts and in the treatment of herpesviruses. Compositions with corticosteroids are more effective than propolis alone because they reduce inflammation associated with viruses causing warts or herpes eruptions.

10 Claims, No Drawings

COMPOSITIONS FOR THE TREATMENT OF WARTS AND HERPES

This application is a continuation in part of copending patent application Ser. No. 08/495,219 filed on Jun. 27, 1995 to be issued on Nov. 19, 1996 as U.S. Pat. No. 5,576,005.

Topical application of propolis is an effective, non-invasive, painless treatment against warts. Mixing propolis with salicylic acid, hydrocortisone or both results in a synergistic effect, achieving a faster resolution of warts compared to results obtained by applying either propolis or salicylic acid. Hydrocortisone reduces inflammation. Propolis compositions are also effective against herpes infections.

Warts are a widespread medical problem that cause pain and discomfort, and may lead to complications if untreated or improperly treated. Warts are benign growths of the skin caused by a virus that involves the epidermis. Five different types of warts are classified by their clinical presentation. (1) verrucae vulgares are common warts that display hyperkeratosis and may occur anywhere except the genital and mucous membranes and plantar surfaces (soles of the feet); (2) verrucae planae are flat warts that usually occur on the face, trunk and extremities; (3) verrucae plantares are warts that occur only on the soles of the feet; (4) condylomata acuminata are venereal warts that occur on the genitals and mucous membranes; (5) premalignant warts (epidermoldysplasia verruciformis) usually occur on the hands and feet and are rare in occurrence.

Wart treatment is not satisfactory. Many treatments of verrucae involve physical destruction of the infected cells. Choice of treatment depends on the location, size, number, type of wart, age and co-operation of the patient. No one treatment modality is uniformly effective.

Antiwart treatments include cryotherapy with liquid nitrogen, caustics and acids such as salicylic acid, lactic acid and trichloroacetic acid which destroy and peel off infected skin. Retinoic acid has been used topically to treat flat warts. Cantharidin is an extract of the green blister beetle that leads to blistering and focal destruction of the epidermis. Induction of allergic contact dermatitis with dinitrochlorobenzene (DNCB) produces local inflammation on warts to which this chemical has been applied.

Chemotherapeutic agents also employed for venereal warts include topically applied popdophyllin resin which is more effective on mucosal surfaces. This composition is contraindicated in pregnancy and the potency of podophyllin preparations may be highly variable. Purified podophyllotoxin is available having activity that is reproducible in vitro. Application of 5-fluorouracil is sometimes used to treat flat warts and condylomata acuminata. Intralesional bleomycin has also been used but may cause extensive tissue necrosis.

Curettage, electrodesiccation, $CO_2$, and lasers are also used to treat warts. These treatment modalities are painful, require anesthia and cause scarring. A new immunomodulator, Imiquimod has recently been used to topically treat genital and perianal warts and is currently under review by the Food and Drug Administration. The ultimate mechanism of this new composition is that it appears to act through the production of cytokines and activation of natural killer cells. According to a recent report, forty percent of the treated immunocompetent patients experienced resolution of their warts compared to the control group (treated with the vehicle alone). Three of sixteen patients who manifested no clinical evidences of warts after treatment developed a recurrence during a ten week follow up period. Subsequent studies of several hundred patients confirm recurrence rates of 40 to 60%.

Salicylic acid in a topical composition is available for the treatment of warts. In this form, salicylic acid is a keratolytic agent that softens the hyperkeratotic areas by dissolving the intra-cellular matrix and enhancing shedding of scales. This composition is non-specific, being also used for the treatment of psoriasis and other hyperkeratotic disorders. Unfortunately, application of salicylic acid is not always effective for wart resolution. Many patients with warts become frustrated while using salicylic acid because it is ineffective, forcing those patients to seek medical consultation. This may result in applying physical or surgical agents to alleviate patient distress.

Warts often are inflamed due to either xerosis, or due to application of caustic topical over-the-counter acid preparations. This results in a swollen, painful lesion that is usually aggravated by further application of acid mixtures that are either purchased over the counter by the patient or prescribed by a physician. Because no effective treatment for inflamed warts without appreciable side effects is yet available, new modalities are needed.

Herpes viruses contain double stranded DNA and have the capacity to establish latent and overt infection in the human host. Herpes simplex virus gains access to the host through the skin. It then infects associated cutaneous neurons and migrates to the sensory route ganglia where a latent infection is established. Primary herpes simplex virus infection may be associated with extensive cutaneous lesions, severe pain and systemic symptoms. In some cases, the primary infection is asymptomatic.

Recurrent human simplex virus infection represents the activation of the latent virus in the sensory ganglia. Virus particles migrate down the nerves to the affected site in the skin where the primary infection previously occurred. Certain factors such as stress, fever, menses, and sun exposure may precipitate recurrent infection. The frequency of recurrent infection varies greatly between individuals. Two types of herpesviruses designated HSV-1 and HSV-2 are very closely related and share approximately 50% homology in their genetic composition. The two types of viruses can be differentiated using immunohistologic techniques to identify type-specific proteins of these viruses. HSV-1is usually associated with oral herpes and HSV-2 with genital herpes, although each virus can affect both sites.

Herpes simplex virus infection can involve any cutaneous surface and may cause significant physical discomfort and embarrassment. The current drug of choice for the treatment of herpes simplex virus infections is acyclovir, which is a nucleoside analog. It is generally safe and effective because of its very specific anti-viral activity. However, not all strains of herpes simplex virus are susceptible to this drug and therapy is expensive. Recently, analogs of acycloir have been introduced into the market which are better absorbed; however, they are even more expensive than acyclovir itself. Consequently, topical preparations which would alleviate discomfort due to cutaneous surfaces, yet be inexpensive, are needed. In-vitro studies investigating the potential of components of propolis as having anti-HSV-1 activity have not resulted in the use of propolis in the treatment of herpes viruses. (Amnoros, 1992).

SUMMARY OF THE INVENTION

An aspect of the present invention is the use of topical propolis compositions for warts, in particular inflamed warts. The compositions include propolis alone, or combined with salicylic acid, hydrocortisone, or salicylic acid and hydrocortisone. The compositions are also effective when applied to lesions of herpes labialis (oral herpes) and herpes genitalis (genital herpes). Blistering eruptions are caused by members of the human herpesvirus family.

An effective, topical wart treatment, particularly to prevent or treat inflammation of warts, is a novel propolis composition. Combining propolis and salicylic acid with a corticosteroid such as hydrocortisone or a halogenated corticosteroid such as triamcinalone in a spreadable vehicle for topical application in treating warts, shows improved effectiveness in reducing inflammation, without reducing effectiveness of a propolis composition topical treatment or a propolis composition including salicylic acid. The present invention relates to adding hydrocortisone or halogenated corticosteroids to the propolis mixture for an effective treatment that resolves the wart and simultaneously provides anti-inflammatory relief. Topical application of propolis compositions are used for successful treatment of the following types of warts: verrucae vulgares, verrucae plantares, condylomata acuminata and verrucae planae.

Compositions used for the topical application include a combination of propolis and salicylic acid with a vehicle, as well as two separate compositions, one including, propolis, the other salicylic acid. Separate compositions are applied sequentially to a wart, at about the same time. Either may be applied first, although the preferred sequence is that propolis is applied first to the wart, then salicylic acid is layered over it. When adding hydrocortisone or a halogenated corticosteroid to a topical application, either a composition of propolis and hydrocortisone, or a composition of propolis, salicylic acid and hydrocortisone is effective. The composition can be combined in a single vehicle or applied sequentially. While either the propolis, salicylic acid, and hydrocortisone compositions or the propolis and hydrocortisone compositions can be applied sequentially in any order, it is preferred that propolis compositions be applied before applying either hydrocortisone alone or hydrocortisone and salicylic acid.

Hydrocortisone is a corticosteroid possessing anti-inflammatory activity and a low potential for inducing side effects such as cutaneous atrophy, telangiectasia and skin fragility. Halogenated corticosteroids have more potent anti-inflammatory activity and a higher chance of inducing the undesirable side effects. Halogenated corticosteroids can safely be used under a doctor's supervision, as long as their application is closely monitored and avoidance of areas susceptible to these side effects is maintained. These areas susceptible to side effects include the facies, breasts, genitalia and glabrous skin.

A composition combining propolis, salicylic acid and hydrocortisone provides excellent improvement of warts that are mildly inflamed, where the skin is slightly red or the patient experiences mild pain or itching. The combination of propolis, salicylic acid and halogenated corticosteroids provides excellent relief of moderate to severely inflamed warts, where the skin is red and swollen, and the patient is experiencing severe pain or itching to the point it distracts the patient from his or her daily activities.

The topical compositions of the present invention not only relieve the discomfort due to the inflammation, but also allow the patient to pursue his or her daily duties without distractions. This allows patients with inflamed verrucae plantares to ambulate normally and to preclude loss of productivity. Similar therapeutic effects result from applying such mixtures to sites having verrucae vulgares and condylomata acuminata.

The application of propolis topically results in the resolution of verrucae vulgares, verrucae plantares and condylomata accuminata. The therapeutic action presumably resulted from the antiviral activity of the propolis. The application of this new composition also is effective against cutaneous lesions caused by herpes labialis and genital herpes.

DESCRIPTION OF THE PREFERRED EMBODIMENTS

Compositions of propolis, and compositions of propolis with salicylic acid and hydrocortisone or halogenated corticosteroids are prepared in a pharmaceutical acceptable topical vehicle. Although the compositions comprising propolis can be used alone in the treatment of warts, combination with superficial cryo-surgery is also possible and desirable in some cases to decrease resolution time in the treatment. The combination of propolis and cryo-surgery produced faster therapeutic results compared to each modality alone. However, cryo-surgery is expensive and invasive.
Composition and Characteristics of Propolis, Salicylic Acid and a Corticosteroid Propolis is a naturally occurring substance made by bees to cement defects in the hive and also to encapsulate insects and other animals that may invade the hive. The encapsulated organisms do not decay, possibly due to antimicrobial and antiviral properties of propolis.

Bees use propolis as a building and repair material. It is used to seal the cracks and irregularities in the hive nest, as well as for "embalming" the bodies of intruders, such as other insects, mice, frogs, snakes, and the like. Propolis (bee glue) is a resin, commonly of dark-green, brown, or dark-brown color. It is solid at 15° C. and becomes soft and pliable at 60–70° C. Its specific gravity is 1.112–1.136. It has a melting temperature in the range of 80–104° C., and it is soluble in alcohol, ether and some other solvents. The main components of propolis are plant tars, ether oils and wax, flavonoids, as well as bee saliva and pollen, iron and trace elements.

Propolis may be obtained from Beehives Botanicals, Wisconsin. The propolis purchased commercially is combined from various sources of beehives in North America. Propolis is generally combined with a solvent for use in the present invention. A suitable solvent is 95% ethyl alcohol which lowers the viscosity of propolis.

A suitable topical vehicle for salicylic acid in a combined or separate composition can include, e.g., white petroleum, mineral oil, Aquaphor®, Eucerin® cream, and any other medium capable of containing the propolis in solution, suspension or emulsion, at all concentrations with salicylic acid suitable to produce an easily applied, "non runny" composition and that will not cause damage to the skin. A preferred composition is 60–70% propolis, 15–20% salicylic acid, and 15–25% Aquaphor® as the vehicle (% are by weight/volume). An even more preferred composition is about 65% propolis, 17% salicylic acid, and 23% Aquaphor®. A composition that is less "runny" and more viscous is preferred.

The application of hydrocortisone or halogenated corticosteroids alone does not render any resolution of warts because these chemicals possess no pharmacologic activity against viruses or warts. Salicylic acid alone does not provide swift and effective resolution of warts when compared to the application of propolis alone. Combinations of the propolis and salicylic acid produce faster and more complete resolution of warts. The addition of hydrocortisone or halogenated corticosteroids decreases the inflammation and allows the other two ingredients to exert their activity against warts while giving patients relief. This also results in better patient compliance because relief of symptoms is hastened. The therapeutic benefit obtained by the addition of the corticosteroids therefore exceeds the benefit of applying propolis alone or propolis mixed with salicylic acid.

A suitable topical vehicle for mixtures of propolis, salicylic acid and hydrocortisone includes white petroleum, mineral oil, Aquaphor®, Eucerin® cream and any other medium capable of containing the propolis in solution, suspension or emulsion, at all concentrations suitable to produce an easily applied "non-runny" composition that will not cause damage to the skin. A preferred composition is 60–70% propolis, 15–20% salicylic acid, 15–25% hydrocortisone (either a powder or a solution in water or propylene glycol) or with 0.1% to 0.5% triamcinalone (powder or a solution in water or propylene glycol).

Various preferred embodiment compositions include the following:
1. 65% propolis, 17% salicylic acid 0.5% hydrocortisone and 17.5% Aquaphor®.
2. 65% propolis, 17% salicylic acid, 1% hydrocortisone and 17% Aquaphor®.
3. 65% propolis, 17% salicylic acid, 2.5% hydrocortisone and 15.5% Aquaphor®.
4. 65% propolis, 17% salicylic acid, 0.1% triamcinalone and 17.9% Aquaphor®.
5. 65% propolis, 17% salicylic acid, 0.5% triamcinalone and 17.5% Aquaphor®.

Preparations containing propolis and hydrocortisone are also effective when applied to painful lesions of herpes labialis and genital herpes. Hydrocortisone has no antiviral activity and does not expedite healing of lesions caused by the herpesviruses. However, when combined with propolis, its anti-inflammatory activity provides relief from the discomfort of pain and itching while the propolis exerts its anti-viral activity. In addition, when salicylic acid is added to mixtures of propolis and hydrocortisone in Aquaphor, it facilities penetration of these ingredients into the affected sites.

Preferred compositions for the treatment of herpesviruses include the following:
1. 65% propolis, 17% salicylic acid 0.5% hydrocortisone and 17.5% Aquaphor.
2. 65% propolis, 17% salicylic acid, 1% hydrocortisone and 17% Aquaphor.
3. 65% propolis, 17% salicylic acid, 2.5% hydrocortisone and 15.5% Aquaphor.

Suitable topical vehicles for the compositions of propolis and corticosteroid include substances, in addition to Aquaphor®, white petroleum, mineral oil, Eucerin® cream, and any other medium capable of containing the propolis, propolis and salicylic acid and propolis, saclicylic acid and a corticosteroid in solution, suspension or emulsion suitable to produce an easily applied composition that will not cause damage to the skin.

Action of Propolis on Warts

Pharmacological actions of propolis are reported and may be due to the presence of large amounts of flavonoid (Pepeljnjak, 1985), particularly galangin and pinocembrine, together with a multitude of others. Flavonoids have a variety of pharmacological effects, some of which have been well studied (Havsteen, 1983).

The possibility exists that propolis acts as an antiviral agent that invades the infected epidermal cells and kills the virus within the cells. In the improved compositions of the present invention, the acidity of salicylic acid may facilitate entry of the propolis into the infected cell by disturbing the intercellular matrix of the wart, dissolving the protein and thus changing the physical-chemical properties of infected cell membranes. Entry of the propolis and/or the salicylic acid then produces a more effective antiviral therapy.

EXAMPLE 1

Treatment of Patients with Compositions Comprising Propolis

Fifty-three patients were treated with a composition comprising propolis. (Table 1) Every patient in the group failed to respond to previous therapeutic modalities that included salicylic acid alone, superficial liquid nitrogen cryosurgery, or a combination of the two.

The study included 53 patients. Twelve had condylomata acuminata, 20 had verrucae vulgares, one had verrucae planae, 20 verrucae plantares. Several had more than one type of wart: 1) two patients had verrucae vulgares and plantares; 2) one had verrucae vulgares and condylomata acuminata; 3) one had verrucae plantares and condylomata acuminata, one had verrucae plantares and condylomata acuminata.

Initially a 10% solution in alcohol as the vehicle (wt. per volume) was used but this was later changed to a 65% (wt. per volume) solution. Generally, 95% ethyl alcohol is preferred. Both concentrations were well tolerated, but the 65% solution was preferred due to its higher viscosity and ease of application. It was thus easier to apply than the less concentrated solution which took more time to dry and dripped more than the 65% solution.

Fifty-three patients were treated with a composition of propolis in alcohol. In 35 of the 53 patients, the warts clinically cleared and were not seen on cutaneous examination. Eight (8) manifested a partial resolution in that the warts were found to have been reduced in bulk and quantity by at least 50%. Five (5) were lost to follow-up. Five showed no response, including the one patient with flat warts, but the warts in the latter patient were easily visualized and this led to efficient electrocautery therapy. Salicylic acid and cryosurgery were not used with this patient because these modalities are not effective in the treatment of verrucae planae. The average length of time of treatment was approximately four months.

Seven patients with plantar warts stated that although their warts were smaller within two months with the application of propolis solution, they desired an even faster therapeutic result. These patients were told to continue to apply the propolis twice daily. In addition these patients were given the prescription of 20% salicylic acid in Aquaphor® ointment to be applied over the propolis. All seven patients manifested complete clinical resolution by visual examination of the warts within two weeks thereafter. For 20% salicylic acid to be applied over the propolis a preferred routine is to apply twice daily.

A composition comprising propolis alone is an effective nonsurgical treatment of warts, because 36 patients out of 53 patients (67%) treated with propolis alone manifested complete resolution of their warts, that is, the warts were not clinically detected by visual examination. Patients treated with propolis alone manifested complete resolution of warts. Seven out of seven patients (100%) treated with the application of propolis and a salicylic acid mixture also manifested complete resolution and did so in approximately half the time as patients treated with propolis alone. A synergistic effect is supported. These patients were treated prior to propolis therapy with 20% salicylic acid in Aquaphor® for at least two months and showed no clinical response to this therapeutic modality. Using the propolis with or without the salicylic acid led to a total of 43 out of 53 patients (81%) to manifest complete resolution, that is, the warts were not clinically detected by visual examination.

TABLE 1

Effect of Propolis on Warts

| Total patients with *Condylomata Acuminata*: 12 | |
|---|---|
| Sex | 12 males |
| Complete Resolution | 4 |
| No Resolution | 3 |
| Lost to follow up | 5 |
| Total patients with *verrucae Vulgaris*: 20 | |
| Sex | 11 males |
|  | 9 females |
| Complete Resolution | 19 |
| No Resolution | 1 |
| Total patients with *verrucae Planae*: 1 | |
| Sex | 1 female |
| Complete Resolution | 0 |
| No Resolution | 1 |
| Total patients with *verrucae Plantares*: 20 | |
| Sex | 12 males |
|  | 8 females |
| Complete Resolution | 7 males |
|  | 5 females |
| Partial Resolution | 5 males |
|  | 3 females |

The 7 males were treated with the application of 65% propolis in alcohol plus 20% salicylic acid in Aquaphor® twice daily.

Complete resolution is defined herein as warts not clinically detected by visual examination. Partial resolution is defined as warts that are reduced in bulk and quantity by at least 50% by visual examination.

EXAMPLE 2
Role of Flavonoids as Mechanism of Action of Propolis

It has been proposed that flavonoids are the active pharmacological agents in propolis. Yugoslavian researchers determined that the amount of two types of flavonoid: galangin and pinocembrine, was directly proportional to the effect of propolis on growth inhibition of *Bacillus subtilis* (Pepeljnjak, 1985). Flavonoids' pharmacological properties are discussed in an article by Havsteen (1983). It appears that flavonoids have a variety of effects on the human body. For example, they produce an anti-inflammatory effect by suppressing prostaglandin synthesis, they block histamine release by suppressing $H^+$-ATPase of mast cells, they relieve local pain by suppressing prostaglandin synthesis, and they even normalize cancer cells in cell culture, presumably by affecting the (Na-K) ATPase pump. Flavonoids have also been shown to have an antiviral effect by suppressing $H^+$-ATPase of lysosomal membranes and preventing the lysis of the viral protein coat necessary for entry of the virus into a cell.

Flavonoids have been shown to have extremely low toxicity in animals. For rats, the $LD_{50}$ is 2–10 g per animal for most flavonoids. Similar doses in humans are quite unrealistic (Havsteen, 1983).

Viral infection remains completely harmless until the protein coat surrounding the nucleic acid has been removed by lysosomal digestion. This process requires fusion of the viral mantle with the lysosomal membrane, which must be aided by a proton ATPase and possibly by phospholipase $A_2$. The former enzyme presumably activates the cathepsins by importing protons, which may weaken the lysosomal membrane. Both of these enzymes are inhibited by flavonoid and similar compounds. Therefore, propolis may inhibit viral penetration of the cells and thereby stop or slow the infection process.

EXAMPLE 3
Treatment of Warts with Propolis and Salicylic Acid

Propolis is prepared in 95% ethyl alcohol at a 65% wt. volume. Salicylic acid is prepared in Aquaphor® at a 20% wt./volume. The propolis composition is applied to the surface of a wart. An amount sufficient to cover the wart is applied (about ½ mg of propolis/cm$^2$).

In a short interval, the salicylic acid composition is applied in similar fashion. The entire procedure is repeated 1–2 times a day until the wart resolves.

The compositions are generally applied 1–2 times a day on each wart. The surface of the wart is covered with the compositions. An effective amount is of the order of 0.5 mg/cm$^2$ of wart surface area, although other amounts are within the scope of the present invention. Amounts are adjusted based on size of the wart and response therapy.

EXAMPLE 4
Treatment of Warts with Propolis, Salicylic Acid and Hydrocortisone

A. Propolis at a 65% wt./volume, salicylic acid at 17% wt./volume, and hydrocortisone at a rate of 0.5% wt./volume is prepared in Aquaphor® ointment at 17.5% wt./volume. The composition is applied topically to the wart surface area once or twice a day. About 0.5 mg of the composition per square centimeter of wart surface area is applied.

B. Propolis at a 65% wt./volume, salicylic acid at 17% wt./volume, and hydrocortisone at a rate of 1% wt./volume is prepared in Aquaphor® ointment at 17% wt./volume. The composition is applied topically to the wart surface area once or twice a daily. About 0.5 mg of the composition per square centimeter of wart surface area is applied.

C. Propolis at a 65% wt./volume, salicylic acid at 17% wt./volume, and hydrocortisone at a rate of 2.5% wt./volume is prepared in Aquaphor® ointment at 15.5% wt./volume. The composition is applied topically to the wart surface area once or twice a daily. About 0.5 mg of the composition per square centimeter of wart surface area is applied.

EXAMPLE 5
Treatment of Warts with Propolis Salicylic Acid and Triamcinalone

A. Propolis at a 65% wt./volume, salicylic acid at 17% wt./volume, and triamcinalone at a rate of 0.1% wt./volume is prepared in Aquaphor® ointment at 17.9% wt./volume. The composition is applied topically to the wart surface area once or twice a daily. About 0.5 mg of the composition per square centimeter of wart surface area is applied.

B. Propolis at a 65% wt./volume, salicylic acid at 17% wt./volume, and triamcinalone at a rate of 0.5% wt./volume is prepared in Aquaphor® ointment at 17.5% wt./volume. The composition is applied topically to the wart surface area once or twice a daily. About 0.5 mg of the composition per square centimeter of wart surface area is applied.

EXAMPLE 6
Treatment of Herpesviruses with Propolis, Salicylic Acid and Hydrocortisone A. Propolis at a 65% wt./volume, salicylic acid at 17% wt./volume, and hydrocortisone at a rate of 0.5% wt./volume is prepared in Aquaphor® ointment at 17.5% wt./volume. The composition is applied topically to the viral surface area once or twice a daily. About 0.5 mg of the composition per square centimeter of viral surface area is applied.

B. Propolis at a 65% wt./volume, salicylic acid at 17% wt./volume, and hydrocortisone at a rate of 1% wt./volume is prepared in Aquaphor® ointment at 17% wt./volume. The composition is applied topically to the viral surface area once or twice a daily. About 0.5 mg of the composition per square centimeter of viral surface area is applied.

C. Propolis at a 65% wt./volume, salicylic acid at 17% wt./volume, and hydrocortisone at a rate of 2.5% wt./volume is prepared in Aquaphor® ointment at 15.5% wt./volume. The composition is applied topically to the viral surface area once or twice a daily. About 0.5 mg of the composition per square centimeter of viral surface area is applied.

DOCUMENTS CITED

Amoros, M. et al. (1992), "Synergistic Effect of Flavones and Flavonols Against Herpes Simplex Virus Type 1 in Cell Culture. Comparison With the Antiviral Activity of Propolis." *J Nat. Prod* 55:1732–1740.

Havsteen, B. (1983) "Flavonoid, a class of natural products of high pharmacological potency." *Biochemical Pharmacology* 32: 1141–1148.

Morfei, A. et al. (1980) "Investigations concerning the action of several chemical and biological agents in HBsAg." *Rev. Roum. Med.-Virol.* 31: 273–278.

Pepeljnjak, S. et al. (1982), "Inhibition of growth and biosynthesis of ochratoxin A in *Aspergillus sulfureous* NRRL 4077 by propolis extract." *Pharmazie* 37: 439–440.

Pepeljnjak, S., et al. (1985) "Flavonoid content in propolis extracts and growth inhibition of *Bacillus subtilis.*" *Pharmazie* 40: 112–123.

We claim:

1. A method for the topical treatment of warts, said method comprising applying an amount of "Propolis, salicylic acid, and a corticosteroid or halogenated corticosteroid", said amount effective in the treatment of warts to an area of the skin having warts.

2. A method for the topical treatment of warts, said method comprising application of an amount of "Propolis, salicylic acid, and a corticosteroid or halogenated corticosteroid" effective for the treatment of warts to an area of skin having warts, wherein said treatment comprises topical application of said composition in a concentration of about 0.5 mg of the composition per square centimeter of wart surface area, said application being done at least once per day.

3. The method of claim 1 wherein the ratio of propolis, salicylic acid, and corticosteroid is approximately 60–70% propolis, 15–20% salicylic acid, and 0.5–2.5% hydrocortisone.

4. The method of claim 1 wherein the ratio of propolis, salicylic acid, and corticosteroid is approximately 60–70% propolis, 15–20% salicylic acid, and 0.1–0.5% triamcinolone.

5. A method for the topical treatment of herpesviruses, said method comprising applying an amount of "propolis, salicylic acid, and a corticosteroid or halogenated corticosteroid", said amount effective in the treatment of herpesviruses to an area of the skin having the virus.

6. A method for the topical treatment of herpesviruses, said method comprising application of an amount of "propolis, salicylic acid, and a corticosteroid or halogenated corticosteroid" effective for the treatment of herpesviruses to an area of skin having the virus, wherein said treatment comprises topical application of said composition in a concentration of about 0.5 mg of the composition per square centimeter of viral surface area, said application being done at least once per day.

7. The method of claim 5 wherein the ratio of propolis, salicylic acid, and corticosteroid is approximately 60–70% propolis, 15–20% salicylic acid, and 0.5–2.5% hydrocortisone.

8. The method of claim 5 wherein the ratio of propolis, salicylic acid, and corticosteroid is approximately 60–70% propolis, 15–20% salicylic acid, and 0.1–0.5% triamcinolone.

9. A method for the topical treatment of herpesviruses, said method comprising applying an amount of propolis, and a corticosteroid, said amount effective in the treatment of herpesviruses to an area of the skin having the virus.

10. A method for the topical treatment of herpesviruses, said method comprising application of an amount of propolis, and a corticosteroid effective for the treatment of herpesviruses to an area of skin having the virus, wherein said treatment comprises topical application of said composition in a concentration of about 0.5 mg of the composition per square centimeter of viral surface area, said application being done at least once per day.

* * * * *